(12) United States Patent
Hurlimann et al.

(10) Patent No.: US 6,522,136 B1
(45) Date of Patent: Feb. 18, 2003

(54) WELL LOGGING TECHNIQUE AND APPARATUS FOR DETERMINING PORE CHARACTERISTICS OF EARTH FORMATIONS USING MAGNETIC RESONANCE

(75) Inventors: Martin D. Hurlimann, Ridgefield, CT (US); Pabitra N. Sen, Ridgefield, CT (US); William E. Kenyon, Ridgefield, CT (US)

(73) Assignee: Schlumberger Technology Corporation, Ridgefield, CT (US)

( * ) Notice: Subject to any disclaimer, the term of this patent is extended or adjusted under 35 U.S.C. 154(b) by 0 days.

(21) Appl. No.: 09/528,881

(22) Filed: Mar. 20, 2000

Related U.S. Application Data

(60) Provisional application No. 60/170,121, filed on Dec. 10, 1999.

(51) Int. Cl.$^7$ .................................................. G01V 3/00
(52) U.S. Cl. ......................................................... 324/303
(58) Field of Search .................................. 324/303, 300

(56) References Cited

U.S. PATENT DOCUMENTS

| | | | |
|---|---|---|---|
| 4,986,272 A | * 1/1991 | Reiderer et al. | 600/410 |
| 5,023,551 A | 6/1991 | Kleinberg et al. | 324/303 |
| 5,055,787 A | 10/1991 | Kleinberg et al. | 324/303 |
| 5,055,788 A | 10/1991 | Kleinberg et al. | 324/303 |
| 5,680,043 A | * 10/1997 | Hurlimann et al. | 324/303 |
| 5,796,252 A | * 8/1998 | Kleinberg et al. | 324/303 |
| 6,023,163 A | * 2/2000 | Flaum et al. | 324/303 |
| 6,049,205 A | * 4/2000 | Taicher et al. | 324/303 |
| 6,094,048 A | * 7/2000 | Vinegar et al. | 324/303 |
| 6,097,184 A | * 8/2000 | Flaum | 324/303 |
| 6,163,153 A | * 12/2000 | Reiderman et al. | 324/314 |
| 6,229,308 B1 | * 5/2001 | Freedman | 324/303 |
| 6,369,567 B1 | * 4/2002 | Song et al. | 324/303 |

OTHER PUBLICATIONS

Callaghan, P.T. *Principles of Nuclear Magnetic Resonance Microscopy.* Clarendon Press, Oxford (1991) pp. 68–76.

Callaghan, P.T. et al. *Diffraction–like Effects in NMR Diffusion Studies of Fluids in Porous Solids.* Nature. vol. 351 (Jun. 6, 1991) pp. 467–469.

Fordham, E.J. et al. *Imaging Multiexponential Relaxation in the (y, $\log_e T_1$) Plane, with Application to Clay Filtration in Rock Cores.* Journal of Magnetic Resonance. Series A, 113 (1995) pp. 139–150.

Hurlimann, Martin D. *Effective Gradients in Porous Media Due to Susceptibility Differences.* Journal of Magnetic Resonance. 131, (1998) pp. 232–240.

(List continued on next page.)

*Primary Examiner*—Edward Lefkowitz
*Assistant Examiner*—Tiffany A. Fetzner
(74) *Attorney, Agent, or Firm*—Martin M. Novack; William B. Batzer; John J. Ryberg

(57) ABSTRACT

A method for determining a characteristic of formations surrounding an earth borehole, includes the following steps: (a) providing a logging device that is moveable through the borehole; (b) producing, from the logging device, a static magnetic field in the formations; (c) transmitting, into the formations, from the logging device, a magnetic pulse sequence and receiving, during the pulse sequence, magnetic resonance spin echo signals; the magnetic pulse sequence having a portion of a pulse acquisition sequence with relatively long pulse spacing times $t_{E,1}$ and another portion of the pulse acquisition sequence with relatively short pulse spacing times $t_{E,2}$; and (d) repeating step (c) with pulse spacing times $t_{E,2}$ that are different than $t_{E,2}$; (e) deriving respective $T_2$ distributions from the spin echo signals obtained during the another portion of the pulse acquisition sequence of step (c) and during the another portion of the pulse acquisition sequence of step (d); and (f) determining the characteristic of the formations from the respective $T_2$ distributions.

41 Claims, 7 Drawing Sheets

OTHER PUBLICATIONS

Kenyon, W.E. *Nuclear Magnetic Resonance as a Petrophyscial Measurement. Nuclear Geophysics.* vol. 6, No. 2, (1992) pp. 153–171.

Kleinberg, R.L. *Well Logging. Encyclopedia of Nuclear Magnetic Resonance.* vol. 8, John Wiley & Sons, Chichester, New York (1996) pp. 4960–4969.

Mansfield, P. *Imaging by Nuclear Magnetic Resonance. Pulsed Magnetic Resonance: NMR, ESR, and Optics.* Clarendon Press, Oxford. (1992) pp. 317–345.

Stejskal, E.O. et al. *Spin Diffusion Measurement: Spin Echoes in the Presence of a Time–Dependent field Gradient. The Journal of Chemical Physics.* vol. 42, No. 1 (1965) pp. 288–292.

* cited by examiner

WELL LOGGING TECHNIQUE AND APPARATUS FOR DETERMINING PORE CHARACTERISTICS OF EARTH FORMATIONS USING MAGNETIC RESONANCE

RELATED APPLICATION

The present application claims priority from U.S. Provisional Patent Application No. 60/170,121, filed Dec. 10, 1999.

FIELD OF THE INVENTION

This invention relates to well logging investigation of subsurface formations and, more particularly, to nuclear magnetic resonance (NMR) methods for determining characteristics of subsurface rock, including their pore characteristics.

BACKGROUND OF THE INVENTION

General background of nuclear magnetic resonance (NMR) well logging is set forth, for example, in U.S. Pat. 5,023,551. Briefly, in NMR operation the spins of nuclei align themselves along an externally applied static magnetic field. This equilibrium situation can be disturbed by a pulse of an oscillating magnetic field (e.g. an RF pulse), which tips the spins away from the static field direction. After tipping, two things occur simultaneously. First, the spins precess around the static field at the Larmor frequency, given by $\omega_0 = \gamma B_0$, where $B_0$ is the strength of the static field and $\gamma$ is the gyromagnetic ratio. Second, the spins return to the equilibrium direction according to a decay time T1, the spin lattice relaxation time. For hydrogen nuclei, $\gamma/2\pi=4258$ Hz/Gauss, so, for example, for a static field of 235 Gauss, the frequency of precession would be 1 MHz. Also associated with the spin of molecular nuclei is a second relaxation, T2, called the spin-spin relaxation time. At the end of a ninety degree tipping pulse, all the spins are pointed in a common direction perpendicular to the static field, and they all precess at the Larmor frequency. However, because of small inhomogeneities in the static field due to imperfect instrumentation or microscopic material heterogeneities, each nuclear spin precesses at a slightly different rate. T2 is a time constant of this "dephasing".

A widely used technique for acquiring NMR data, both in the laboratory and in well logging, uses an RF pulse sequence known as the CPMG (Carr-Purcell-Meiboom-Gill) sequence. As is well known, after a wait time that precedes each pulse sequence, a ninety degree pulse causes the spins to start precessing. Then, a one hundred eighty degree pulse is applied to keep the spins in the measurement plane, but to cause the spins which are dephasing in the transverse plane to reverse direction and to refocus. By repeatedly reversing the spins using one hundred eighty degree pulses, a series of "spin echoes" appear, and the train of echoes is measured and processed.

The determination of the characteristics of the pores in subsurface rock formations is an important goal of NMR logging. Statistical description of the pore space is useful in understanding commercially important properties of the formations, such as permeability to fluid flow.

Existing NMR relaxation techniques typically determine $T_1$ or $T_2$ distributions which arise from surface relaxation. [For background, reference can be made, for example, to W. E. Kenyon, Nucl Geophys. 6, 153, 1992; R. L. Kleinberg, in "Encyclopedia of Nuclear Magnetic Resonance", Wiley, N.Y., 1995; E. O. Stejskal and J. E. Tanner, J. Chem. Phys. 42, 288, 1965; P. T. Callaghan, A. Coy, D. MacGowan, K. J. Packer and F. O. Zelaya 351, 467, 1991).] The data is generally analyzed in terms of distribution of ($\rho$S/V), where $\rho$ is the surface relaxivity and S/V is surface to volume ratio. The resulting pore size distribution is used, in turn, to obtain permeability, FFI (free fluid index), etc. While generally successful, this method suffers from $\rho$ being unknown and subject to wettability conditions. A few monolayers of an absorbent on the grains can change the surface relaxivity $\rho$ completely. There is also uncertainty regarding the proper cutoff to be used in estimating FFI.

It is among the objects of the present invention to provide an NMR well logging technique that can determine pore characteristics of formations, independent of wettability.

SUMMARY OF THE INVENTION

A form of the present invention includes a technique for discriminating and analyzing components of fluids using internal field gradient as a measure of pore size in rocks, substantially independent of wettability. When a porous material is subjected to a uniform external magnetic field, an inhomogeneous magnetic field may appear inside the pore space, due to the contrast of the magnetic susceptibility between the solid materials and the pore-filling fluid. The inhomogeneity of this internal field can be rather large in sedimentary rocks (see M. D. Hurlimann, J. Magn. Res. 131, 232–40, 1998).

As noted above, wettability can have a profound effect on surface reflectivity, resulting in uncertainty in determination of formation characteristics including pore size distribution, permeability, and free fluid index. In contrast, the strength of internal gradients are little affected by wettability. Therefore, NMR methods based on surface relaxation and internal gradients react differently to wettability changes.

A form of the present invention uses the decay due to the internal gradients g as a probe of the pore size. In a simple model, the strength of the internal gradient g is proportional to the applied field $B_0$ times the susceptibility difference $\Delta_\chi$ between grain and fluid divided by the pore-size $l_p$, i.e.

$$g \propto \frac{\Delta_\chi B_o}{l_p}$$

Thus, g has pore size information. $\Delta_\chi$ may be a constant to be determined from cuttings or correlations. At short times, the decay of transverse magnetization in the presence of g is well known. This gives a direct correlation between the decay in the presence of the gradient and the poresize.

The total NMR decay is influenced both by surface relaxation and diffusion in internal gradients. By partitioning the time of evolution into two sectors and varying them systematically, the two processes can be separated.

In an accordance with an embodiment of the invention, there is set forth a method for determining a characteristic of formations surrounding an earth borehole, comprising the following steps: (a) providing a logging device that is moveable through the borehole; (b) producing, from the logging device, a static magnetic field in the formations; (c) transmitting, into the formations, from the logging device, a first magnetic pulse sequence and receiving, during the first pulse sequence, magnetic resonance spin echo signals; the first pulse sequence having a portion during which spin echoes are subject to decay due to local magnetic field gradients in the formations, and having another portion during which spin echoes are not substantially subject to decay due to the local magnetic field gradients in the formations; (d) transmitting, into the formations, from the logging device, a second magnetic pulse sequence and receiving, during the second pulse sequence, magnetic resonance spin echo signals; the second pulse sequence having a portion during which spin echoes are subject to decay due to the local magnetic field gradients in the formations, and having another portion during which spin echoes are not substantially subject to decay due to the local magnetic field gradients in the formations; one of the portions of the second magnetic pulse sequence having at least one different pulse parameter than the corresponding one of the portions of the first magnetic pulse sequence; and (e) determining said characteristic of the formations from the spin echo signals of the first pulse sequence and the spin echo signals of the second pulse sequence.

In one embodiment of the invention, the different pulse parameter comprises respectively different pulse spacings, and in another embodiment of the invention the different pulse parameter comprises different durations of the respective another portions of the first and second magnetic pulse sequences.

In an embodiment of the invention, said another portion of the respective first and second magnetic pulse sequences comprise successive CPMGs, the CPMG pulse spacing of said portion being much longer than the CPMG pulse spacing of said another portion of the respective first and second magnetic pulse sequences. In this embodiment, the step (e) includes deriving a first $T_2$ distribution from the spin echo signals of said first magnetic pulse sequence and deriving a second $T_2$ distribution from the spin echo signals of said second magnetic pulse sequence, and further includes deriving, from the first and second $T_2$ distributions, at particular values of $T_2$, the product $g^2D$ where g is magnetic field gradient and D is the diffusion constant of the formation fluid. Also in this embodiment, the step (c) can further includes deriving a formation pore size distribution from values of $g^2D$, and also deriving formation permeability.

Further features and advantages of the invention will become more readily apparent from the following detailed description when taken in conjunction with the accompanying drawings.

DETAILED DESCRIPTION

Figure 1:
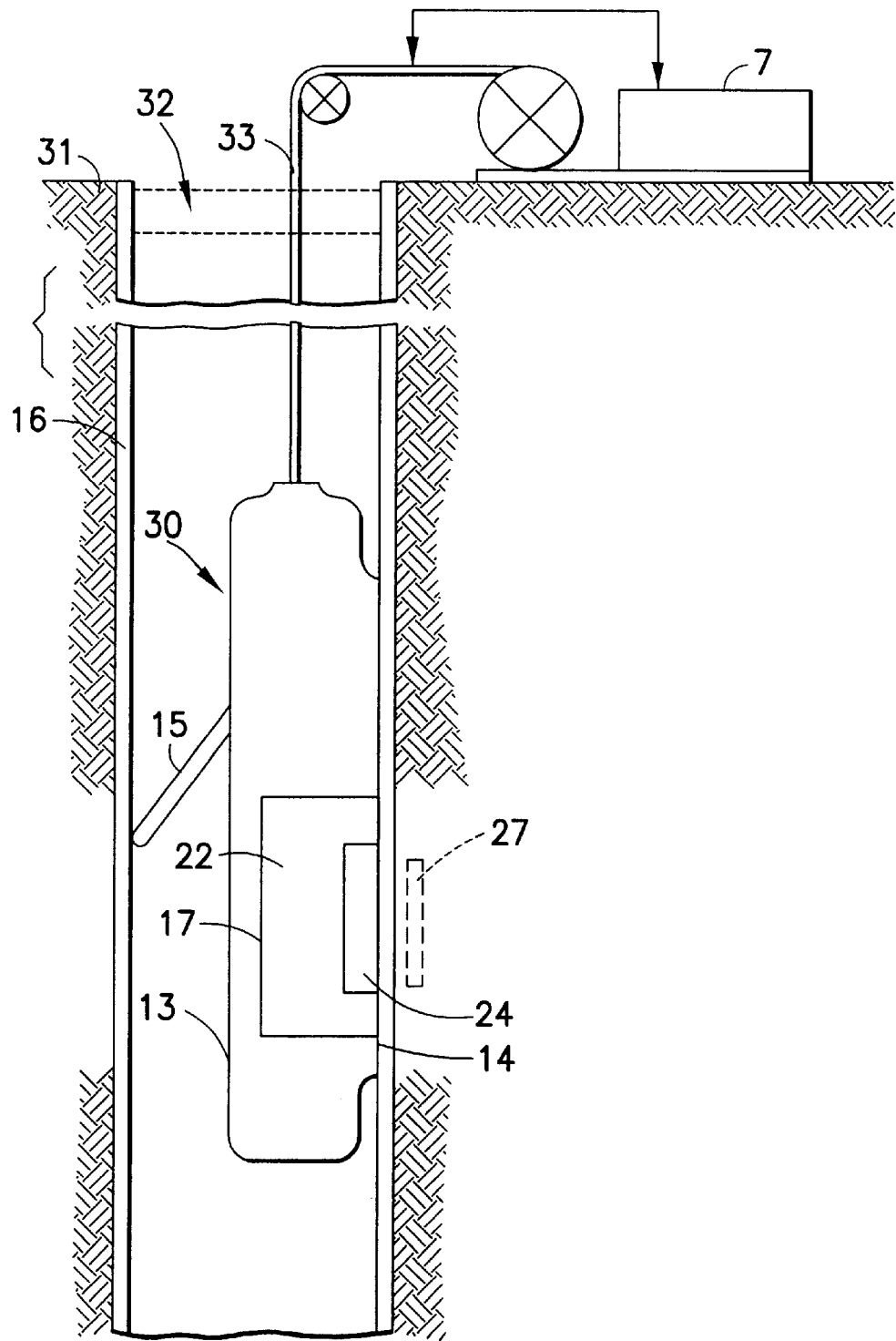
FIG. 1 is a schematic diagram, partially in block form, of a well logging apparatus that can be used in practicing embodiments of the invention.

Referring to FIG. 1, there is shown an apparatus that can be utilized for investigating subsurface formations 31 traversed by a borehole 32 and for practicing an embodiment of the invention. A magnetic resonance investigating apparatus or logging device 30 is suspended in the borehole 32 on an armored cable 33, the length of which substantially determines the relative depth of the device 30. The length of cable 33 is controlled by suitable means at the surface such as a drum and winch mechanism (not shown). Surface equipment, represented at 7, can be of conventional type, and can include a processor subsystem and communicates with all the downhole equipment. It will be understood that processing can be performed downhole and/or uphole, and that some of the processing may be performed at a remote location. Also, while a wireline is illustrated, alternative forms of physical support and communicating link can be used, for example in a measurement-while-drilling system. As described for example in the U.S. Pat. No. 5,055,787, the magnetic resonance logging device 30 can have a face 14 shaped to intimately contact the borehole wall, with minimal gaps or standoff. The borehole wall may have a mudcake 16 thereon. A retractable arm 15 is provided which can be activated to press the body of the tool 13 against the borehole wall during a logging run, with the face 14 pressed against the wall's surface. Although the tool 13 is shown as a single body, the tool may alternatively comprise separate components such as a cartridge, sonde or skid, and the tool may be combinable with other logging tools.

The logging device includes, for example, a permanent magnet or permanent magnet array 22, which may comprise samarium-cobalt magnetic material, and one or more RF antennas 24. The investigation region, or sensitivity zone, represented generally at 27, is a region in the formations in which the static magnetic field is generally uniform, except for local gradients, although this is not necessarily required for operation in accordance with embodiments of the invention. It will be understood that other suitable tool configurations can be utilized.

Figure 2:
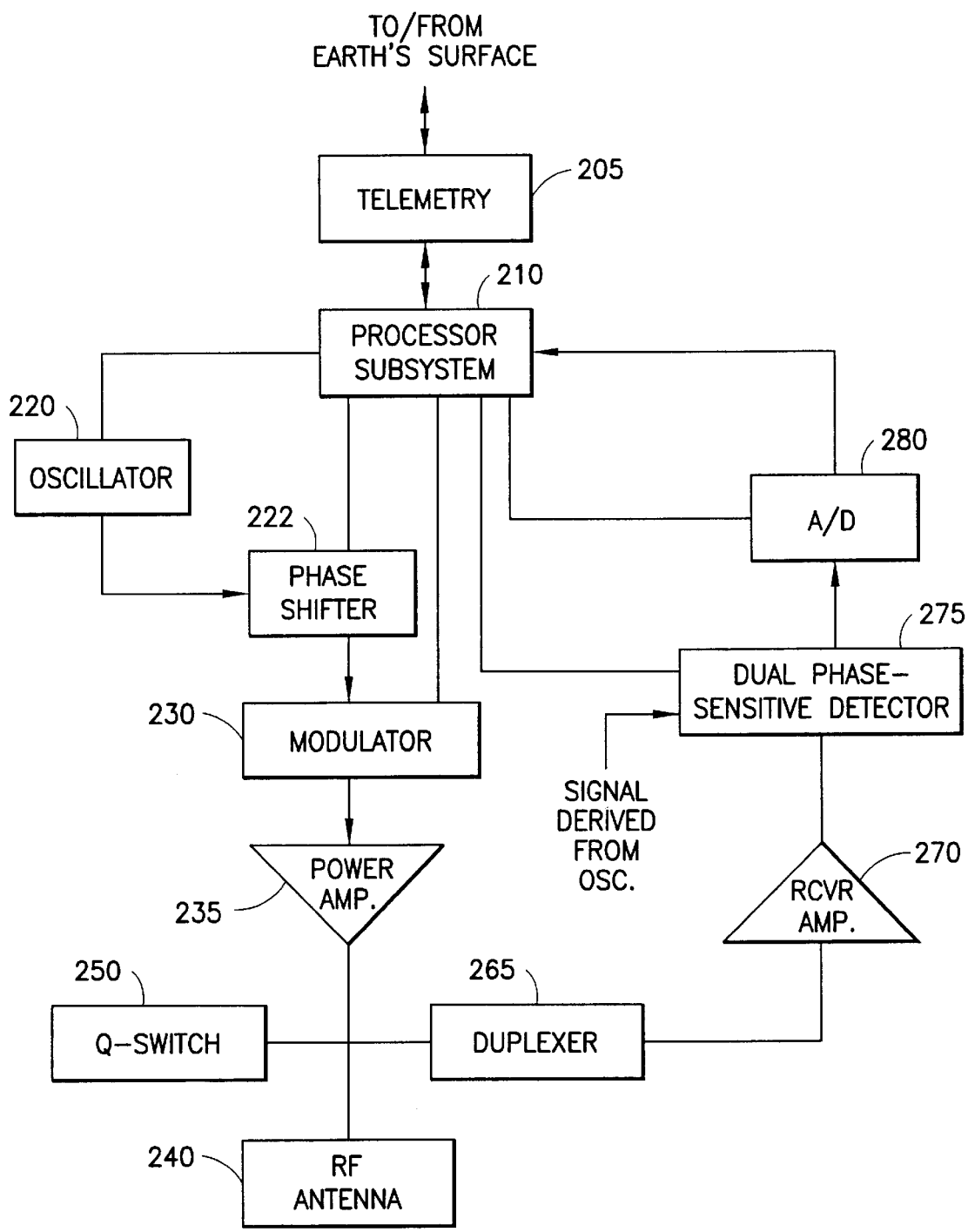
FIG. 2 is a block diagram of downhole circuitry of the FIG. 1 apparatus.

FIG. 2 shows, in simplified form, circuitry of a type that can be used for producing RF pulse sequences and for receiving and processing NMR signals. In the Figure diagram, a downhole processor subsystem is represented at 210. The processor subsystem 210 has associated memory, timing, interfaces, and peripherals (not separately shown), as is well known in the art. The processor subsystem is conventionally coupled with telemetry circuitry 205, for communication with the earth's surface. An oscillator 220 produces radio frequency (RF) signals at the desired resonant frequency or frequencies in the investigation region, and the output of the oscillator is coupled to a phase shifter 222 and then to a modulator 230, both of which are under control of the processor subsystem 210. The phase shifter and modulator can be controlled, in a manner known in the art, to produce the desired pulses of RF field, for example the 90 degree and 180 degree pulses utilized in embodiments hereof. As described, for example, in the U.S. Pat. No. 5,055,788, the oscillator 220 can be a plurality of oscillators used in a manner that facilitates the generation and ultimate detection of the desired signals. The output of modulator 230 is coupled, via a power amplifier 235, to the RF antenna 240. A Q-switch 250 can be provided to critically damp the RF antenna system to reduce antenna ringing. The antenna 240 is also coupled with a receiver section via duplexer 265, the output of which is coupled to receiver amplifier 270. The duplexer 265 protects the receiver amplifier 270 from the high power pulses which pass to the RF antenna 240 during the transmitting and damping modes. During the receiving mode, the duplexer 265 is effectively just a low impedance connection from the antenna to the receiver amplifier 270. The output of the receiver amplifier 270 is coupled to a dual phase-sensitive detector 275, which also receives, as a reference, a signal derived from the oscillator signal. The detected output is coupled to analog-to-digital converter 280, the output of which is a digital version of the received nuclear magnetic resonance signal.

Figure 3:
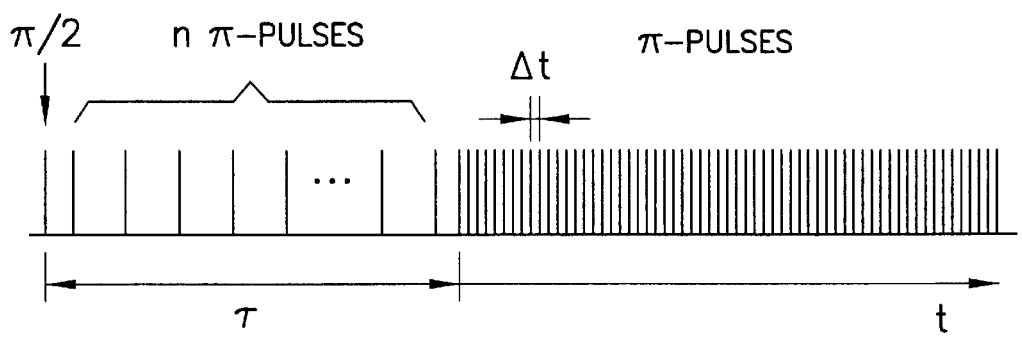
FIG. 3 is a diagram illustrating a magnetic pulse sequence in accordance with an embodiment of the invention.

Consider the pulse sequence illustrated in FIG. 3, which can be produced, for example, using circuitry of the type shown in FIG. 2. In a first portion of the pulse sequence, as in a CPMG sequence, a 90 degree ($\pi/2$) pulse tips the spins into the measurement plane. Then, after a time $\tau/2n$, a 180 degree ($\pi$) reversing pulse is applied, followed by an echo after a time $\tau/2n$, and then repeat of this sequence for a total of n $\pi$-pulses. As seen, during the first portion of the pulse sequence, which has a total time duration of $\tau$, the pulse spacing between 180 degree pulses is about $\tau/n$. In a second CMPG-type portion of the pulse sequence, the 180 degree reversing pulses are continued, during a further running elapsed time t, with a relatively shorter pulse spacing (preferably much shorter, meaning less than half for purposes hereof) than was used during the first portion of the pulse sequence. The pulse spacing during the second portion of the pulse sequence is designated $\Delta t$. The pulse sequence of FIG. 3 can be represented as; $\pi/2$-$\tau/2n$-$\pi/2n$-echo-$\tau/2n$-$\pi$-$\tau/2n$-echo . . . . echo-$\Delta t/2$-$\pi$-$\Delta t/2$-echo-$\Delta t/2$-$\pi$-$\Delta t/2$-echo . . . . In the FIG. 3 pulse sequence, the first portion makes the received signals sensitive to internal field gradients and the second portion makes the signal sensitive to $T_2$ decay. All of the echoes of the second portion of the pulse sequence are acquired. [The echoes of the first portion of the pulse sequence can optionally be acquired.]

In the equations to follow, the echo spacing of the first portion of the magnetic pulse sequence ($\tau/n$ above) is designated $T_{E,1}$, and the echo spacing of the second portion of the magnetic pulse sequence ($\Delta t$ above) is designated $T_{E,2}$. The echo amplitude of the second portion of the sequence (also called the second CPMG), measured at time t (see FIG. 3), which starts at the beginning of the second CPMG, is given by:

$$M(t) = \int\int dT_2 d(g^2 D) f(T_2, g^2 D) \exp\left\{-\frac{1}{12}\gamma^2(g_k^2 D_k)t_{E,1}^2\tau\right\}$$
$$\exp\left\{-\frac{\tau}{T_{2,j}}\right\} \times \exp\left\{-\frac{1}{12}\gamma^2(g_k^2 D_k)t_{E,2}^2 t\right\} \exp\left\{-\frac{t}{T_{2,j}}\right\}$$
$$\approx \int dT_2 \left[\int d(g^2 D) f(T_2, g^2 D) \exp\left\{-\frac{1}{12}\gamma^2(g_k^2 D_k)t_{E,1}^2\tau\right\}\right.$$
$$\left.\exp\left\{-\frac{\tau}{T_{2,j}}\right\}\right] \times \exp\left\{-\frac{t}{T_{2,j}}\right\}$$

In the last step, the assumption is made that $t_{E,2}$ is much shorter than $t_{E,1}$ and that diffusion effects can therefore be neglected during the second CPMG. The quantity $f(T_2, g^2 D)$ is the two dimensional distribution function of the relaxation time $T_2$ and the diffusion parameter $g^2 D$, the product of the square of the local gradient and the diffusion coefficient. In cases when the local gradient is completely dominated by the known applied tool gradient, then this distribution function is directly related to the two-dimensional distribution function of relaxation time and diffusion coefficient. In cases when the fluid is known in the pore space, i.e. the diffusion coefficient is known, $f(T_2, g^2 D)$ can be directly related to the two dimensional distribution function of relaxation time and local gradient. [It will be understood that if the applied gradient (e.g. the static field applied by the logging tool) is known and is relatively much larger than the internal gradient, the diffusion coefficient, D, of the formation fluid, can be determined. The determined diffusion constant can be utilized as a fluid indicator, for example to distinguish between water, gas, light oil, and heavy oil.]

In the measurement cycle of this embodiment, the length of the first CPMG, a, the second echo spacing, $t_{E,2}$, and the duration of the second CPMG are fixed. Then, subsequent measurements are performed with different initial echo spacings, $t'_{E,1}$; that is, at least two different values of $t_{E,1}$. The data for this embodiment is analyzed as follows: For a given initial echo spacing $t_{E,1}$ an inverse Laplace transform is performed, giving a so-called $T_2$ distribution. The amplitude for a particular relaxation time $T_{2,j}$ is given by:

$$h(T_{2,j}) = \left[\int d(g^2 D) f(T_{2,j}, g^2 D) \exp\left\{-\frac{1}{12}\gamma^2(g_k^2 D_k)t_{E,1}^2\tau\right\}\right] \exp\left\{-\frac{\tau}{T_{2,j}}\right\}$$

After multiplication by exp $$\exp\left\{-\frac{\tau}{T_{2,j}}\right\}$$

to compensate for relaxation during the initial CPMG sequence, the dependence of the corrected amplitudes with respect to the initial echo spacing, $t_{E,1}$, can be analyzed. By taking several measurements with different $t_{E,1}$, the data can be inverted to obtain the two dimensional distribution $f(T_2, g^2 D)$.

Figure 4:
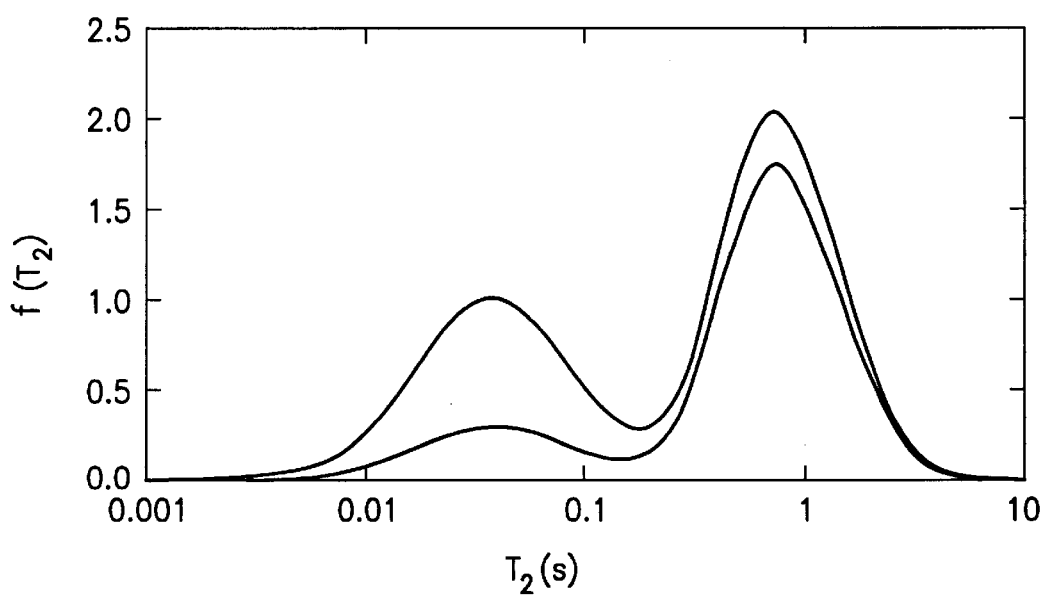
FIG. 4 is a diagram of $T_2$ distributions of a type that are obtained using embodiments of the invention.

FIG. 4 illustrates the expected type of $T_2$ distribution curves for a situation with minimum diffusion editing (top curve—shorter $t_{E,1}$) and substantial diffusion editing (bottom curve—longer $t'_{E,1}$). In this situation, the shorter $T_2$ components are generally more attenuated than the long $T_2$ components; that is, they are subject to larger diffusion effects. Such a cause would be expected when the internal gradients are responsible for the diffusion effects. Namely, larger pores correspond to long $T_2$ and smaller internal gradients (with smaller diffusion effects), and smaller pores correspond to short $T_2$ and larger internal gradients (with larger diffusion effects). At any $T_2$, the function can be evaluated, and pore size distribution and permeability can be derived from the distribution of gradients.

Figure 5A:
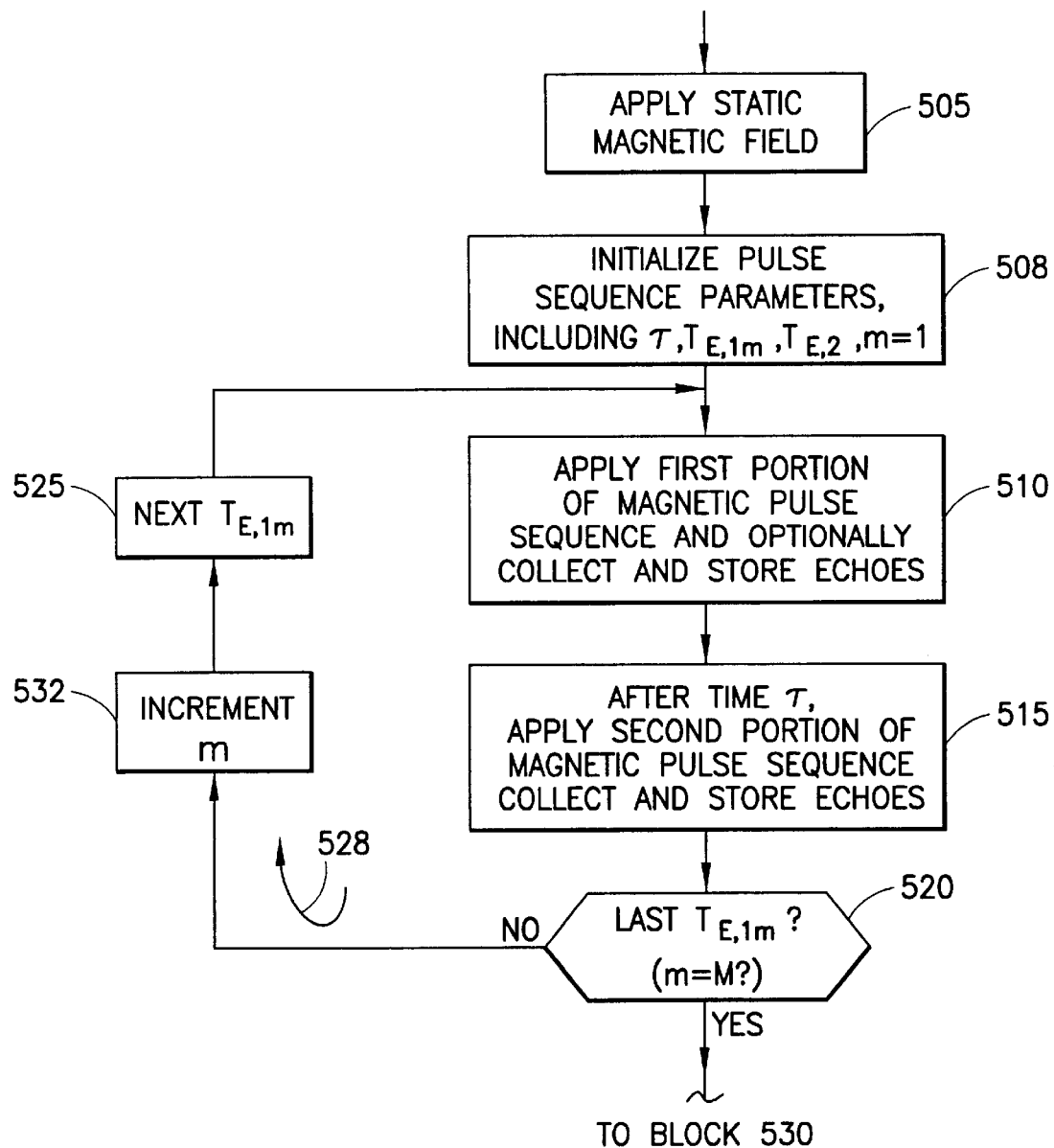
FIG. 5, which includes FIGS. 5A and 5B placed one below another, is a flow diagram of a routine which can be used in programming a processor or processors in implementing embodiments of the invention.
Figure 5B:
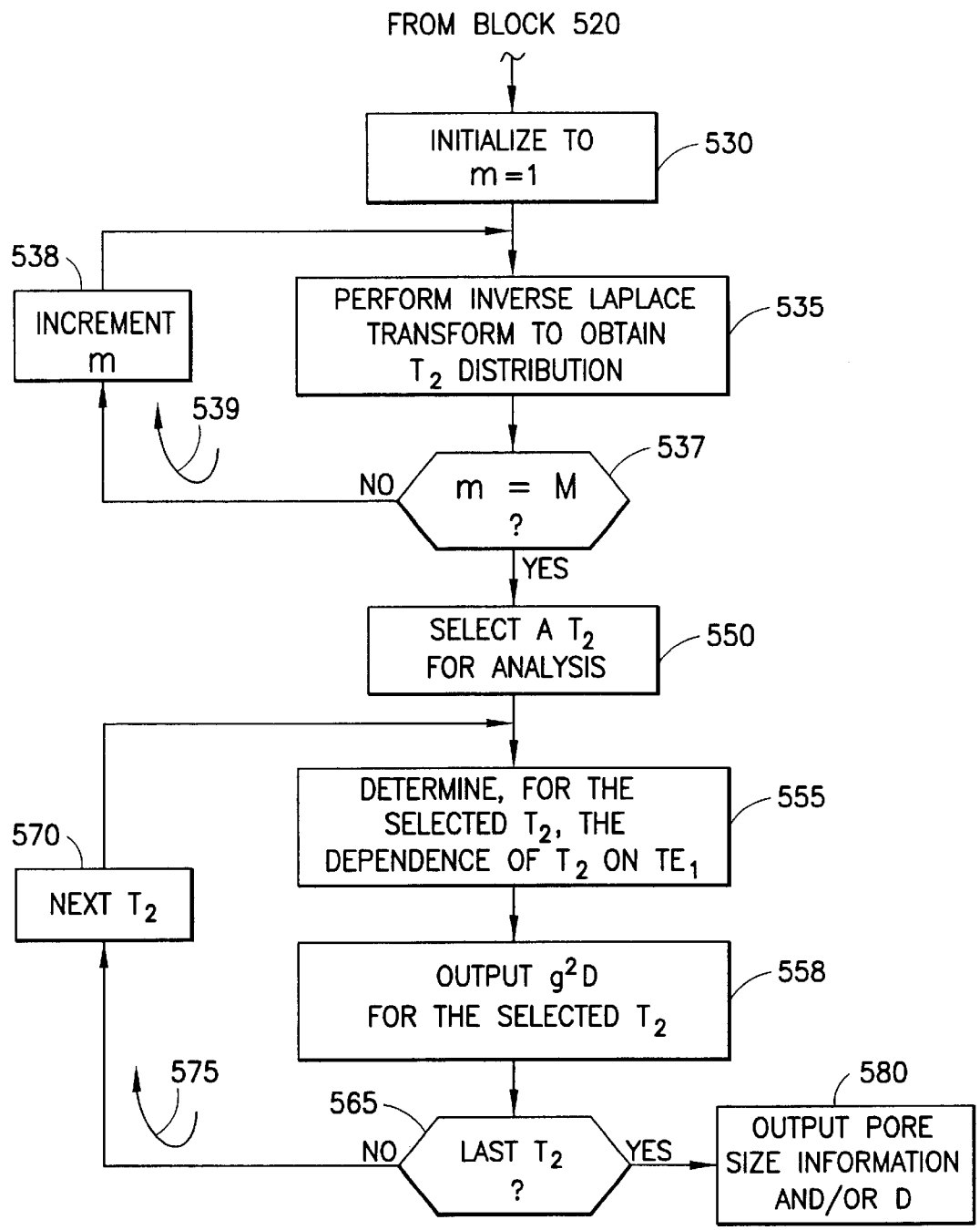

Referring to FIG. 5, there is shown a flow diagram of a routine which can be used in programming a processor or processors in implementing embodiments of the invention. The processor may be, in the FIG. 1 embodiment, the downhole processor, the uphole processor, or a combination thereof. A remote processor may also be used for implementing the data interpretation parts of the routine. The block 505 represents applying a static magnetic field to the region of earth formations surrounding a borehole that is under investigation. [Theoretically, in a situation where there is a high magnetic susceptibility contrast, the earth's magnetic field could be used as the static field; but in most practical situations, this is not preferred.] The block 508 represents initializing pulse parameters for the magnetic pulse sequence, including, for example, $\tau$, $t_{E,1m}$ (m initially 1), and $t_{E,2}$. Next, the block 510 represents applying the first portion of the magnetic pulse sequence which, in this embodiment, is the above-described first portion of the magnetic pulse sequence of FIG. 3, and optionally collecting and storing the echoes. Then, after the time $\tau$ has elapsed, and as represented by the block 515, the second portion of the magnetic pulse sequence is applied, and the echoes are collected and stored. Inquiry is then made (decision block 520) as to whether the last of the series of magnetic pulse sequences has been applied; that is, whether m=M, where M is the number of pulse sequences in the series. In the present embodiment, two or more pulse sequences can be used, so M is originally set at 2 or greater. If m does not yet equal to M, m is incremented (block 522), and the value of $t_{E,1m}$ is set (block 525) for the next magnetic pulse sequence. The block 510 is then re-entered, and the next magnetic pulse sequence is implemented. The loop 528 continues until m=M.

After completion of data collection, the index m is again initialized at 1 (block 530), for consideration of the data of the first magnetic pulse sequence, and a $T_2$ distribution is developed for the data from the second portion of the magnetic pulse sequence, as represented by the block 535. As is known in the art, an inverse Laplace transform technique, for example, can be applied to the echo signals to obtain the $T_1$ distribution. Reference can be made, for example, to E. J. Fordham, A. Sezginer, and L. D. Hall, J. Magn. Reson. A 113, 139–150, 1995. Determination is then made (decision block 537) as to whether the last m (that is, m=M) has been reached. If not, m is incremented (block 538), the block 535 is re-entered, and the next $T_2$ distribution is determined, for the data that had been obtained using the present $t_{E,1m}$. The loop 539 then continues until m=M, with each $T_2$ distribution being determined.

During the next part of the routine, the two dimensional distribution function, $F(T_2,g^2D)$ can be analyzed to determine local gradient, diffusion constant, and pore size information, depending on available information. A particular $T_2$ is selected for analysis (block 550). For the selected $T_2$, the dependence of $T_2$ on $t_{E,1}$ is determined (block 555). As described above, this dependence is a function of $g^2D$, and the block 558 represents the outputting of $g^2D$ for the selected $T_2$. When, for example, the pore fluid is known with some confidence, this output can be used to obtain local gradient, which can be related to pore size, independent of wettability. Conversely, the output can be utilized in determination of diffusion constant under conditions where magnetic field gradient is known. The block 565 then represents determination of whether the last $T_2$ to be selected has been reached. If not, the next $T_2$ is selected for analysis(block 570), the block 555 is re-entered, and the loop 575 continues until all desired $T_2$ values have been analyzed. Pore size information and/or diffusion constant information can then be output, as represented by the block 580.

Figure 6:
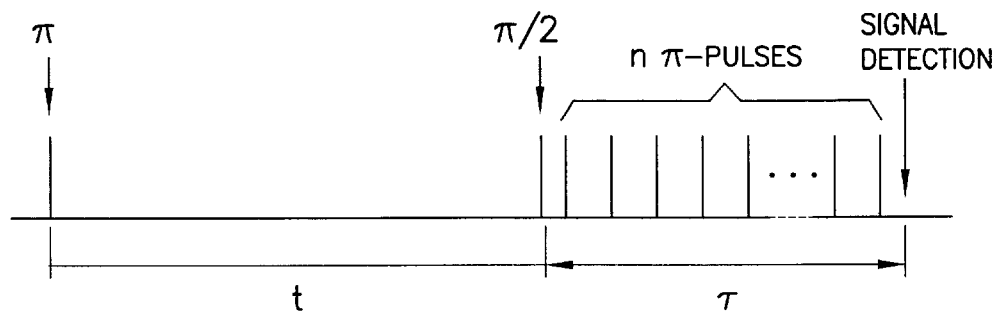
FIG. 6 is a diagram illustrating a magnetic pulse sequence in accordance with another embodiment of the invention.

Referring to FIG. 6, there is shown a magnetic pulse sequence that can be used in practicing a further embodiment of the invention. The pulse sequence can be represented as: $\pi$-t-$\pi$/2-$\tau$/2n-$\pi$-$\tau$/2n-echo-$\tau$/2n-$\pi$ . . . . $\pi$-$\tau$/2n-signal detection. As seen, in this embodiment a CPMG type of pulse sequence is tagged onto a so-called "inversion recovery" pulse sequence (see, for example, P. T. Callaghan, "Principles Of Nuclear Magnetic Resonance", Clarendon Press, Oxford, 1991, for background regarding inversion recovery sequences) in which a 180 degree inverting pulse is followed, after a given time, by a 90 degree pulse that puts the spins into the measurement plane. After the initial $\pi$ pulse, the magnetization recovers as $$M_o \sum_i A_i (1 - 2e^{-t/T_{1i}})$$

Thus, the faster the decay rate, the sooner the magnetization recovers. Then, the amplitude of the nth echo of the CPMG sequence that follows (i.e., at "signal detection" of the foregoing sequence) is given by $$M_o \sum_i A_i (1 - 2e^{-t/T_{1i}}) e^{-\frac{1}{12} D_o \gamma^2 g_i^2 \frac{\tau^3}{n^2}} e^{-\frac{\tau}{T_{2,i}}}$$

Figure 7:
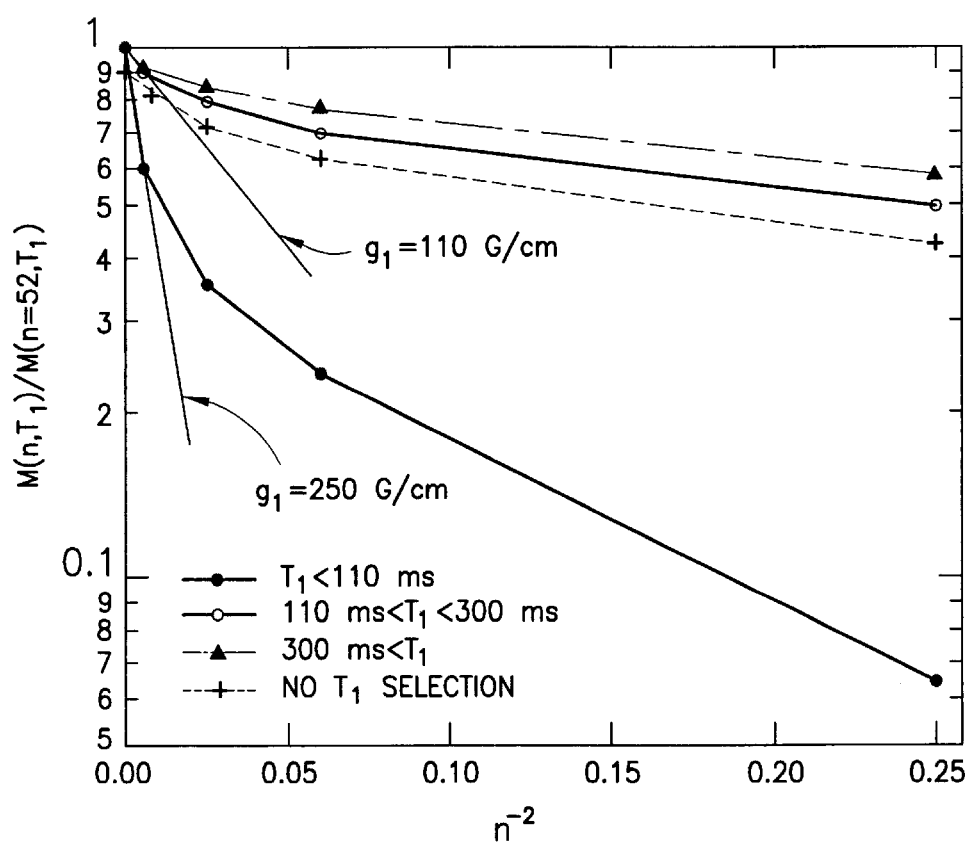
FIG. 7 is a graph that is helpful in illustrating operation of the FIG. 6 embodiment.

The total signal can be analyzed as above by first making a decomposition with respect to t to obtain a $T_1$ distribution. Assuming a known T1/T2 ratio, a distribution of g can be obtained from measurements at different n (or $\tau$), that is, by varying $t_{E,1m}$, as above. FIG. 7 shows some results on a sandstone obtained at 85 MHz. The factors $$e^{-\frac{1}{12} D_o \gamma^2 g_i^2 \frac{\tau^3}{n^2}} e^{-\frac{\tau}{T_{2,i}}} \approx e^{-\frac{1}{12} D_o \gamma^2 g_i^2 \frac{\tau^3}{n^2}}$$

for spins with different $T1_i$ are plotted as a function of $n^{-2}$. It is found, in general, and as expected, that the internal gradient effects are stronger in smaller pores where $T_1$ is also shorter.

For some applications, it will not be necessary to map out the whole gradient distribution, and this permits the measurement strategy to be more economical. If a cut off value for the gradient strength is established, pulse sequences that are effectively only responding to spins with gradients smaller than this cut off value, i.e. spins in pores larger than the corresponding cut off length, can be devised. For a more general case, this gradient editing can be combined with an upper $T_1$ cut off.

Figure 8:
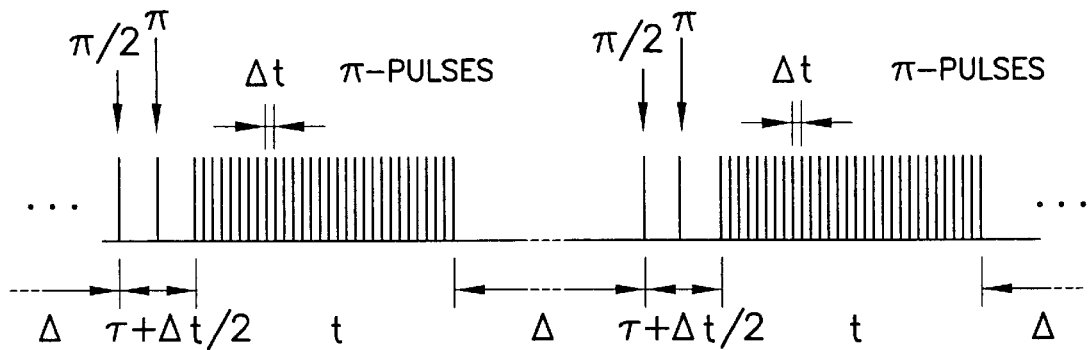
FIG. 8 is a diagram illustrating a magnetic pulse sequence in accordance with another embodiment of the invention.

In some applications, the permeability estimate is improved by eliminating the contribution from very big pores, in particular from vugs with long $T_1$. A pulse sequence that detects only spins in such a size range is illustrated in FIG. 8. The sequence includes a Hahn spin echo with pulse spacing $\tau$/2 (see P. T. Callaghan, "Principles Of Nuclear Magnetic Resonance", Clarendon Press, Oxford 1991 for background regarding the Hahn spin echo pulse sequence), followed by a CPMG sequence with pulse spacing $\Delta t$ and then repeated after a recovery time $\Delta$. The echo amplitudes of the CPMG sequence at time t are given by:

$$M_o \sum_i A_i (1 - 2e^{-\Delta/T_{1i}}) \left( e^{-\frac{1}{12} D_o \gamma^2 g_i^2 \tau^3} e^{-\frac{\tau}{T_{2,i}}} \right) \left( e^{-\frac{1}{12} D_o \gamma^2 g_i^2 \Delta t^2 t} e^{-\frac{t}{T_{2,i}}} \right)$$

The $T_1$ cut off can be controlled by $\Delta$ and the cut off in gradient strength by $\tau$. The pulse spacing $\Delta t$ should be chosen short enough so that the diffusion term in the last bracket can be ignored. This sequence can be combined with the standard CPMG sequence with short echo spacing, which detects the total porosity.

Figure 9:
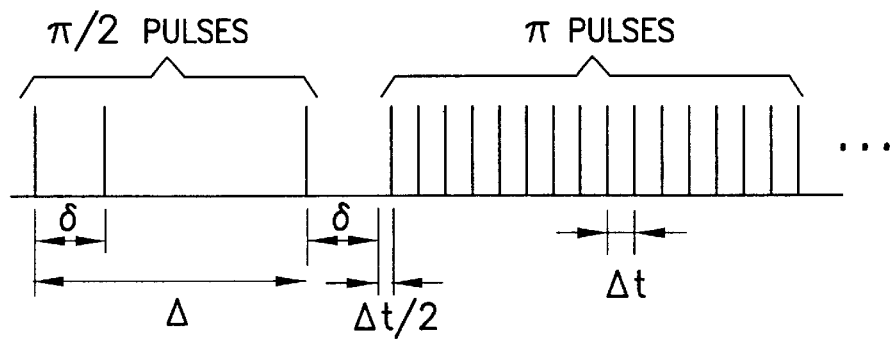
FIG. 9 is a diagram illustrating a magnetic pulse sequence in accordance with another embodiment of the invention.

In a further embodiment of the invention, a pulse sequence is provided (FIG. 9) that includes an initial stimulated echo sequence (see, for example, P. T. Callaghan, "Principles Of Nuclear Magentic Resonance", Clarendon Press, Oxford, 1991, for background regarding stimulated echo sequences), followed by a standard type of CPMG detection. In this embodiment, the stimulated echo sequence consists of three $\pi$/2 pulses at time 0, $\delta$, $\Delta$. This sequence produces a stimulated echo at time $\Delta+\delta$. The amplitude of the stimulated echo depends on diffusion effects by:

$$\frac{1}{2}\exp\{-\gamma^2 g^2 D\delta^2(\Delta-\delta/3)\}.$$

The stimulated echo is then refocused by multiple n pulses analogous to the CPMG sequence. The overall sequence can be written as: $\pi/2$-$\delta$-$\pi/2$-$(\Delta$-$\delta)$-$\pi/2$-$\delta$(stimulated echo)-$\Delta t/2$-$\pi$-$\Delta t/2$-(echo)-$\Delta t/2$-$\pi$-$\Delta t/2$-(echo) . . .

The echo amplitude is given by $$\frac{1}{2}M_o\sum_i A_i\left(e^{-\gamma^2 g_i^2 D_o \delta^2(\Delta-\delta/3)} e^{-\frac{2\delta}{T_{2,i}}-\frac{\Delta-\delta}{T_{1,i}}}\right)\left(e^{-\frac{n\Delta t}{T_{2,i}}} e^{-\frac{1}{12}D_o\gamma^2 g_i^2 \Delta t^3 n}\right) \approx$$

$$\frac{1}{2}M_o\sum_i A_i\left(e^{-\gamma^2 g_i^2 D_o \delta^2 \Delta} e^{-\frac{\Delta}{T_{1,i}}}\right)e^{-\frac{n\Delta t}{T_{2,i}}}$$

In this implementation, two acquisitions are made. The first one with pulse spacing $\delta=\delta_1$, followed by a second acquisition with identical pulse parameters, except $\delta=\delta_2$. From these measurements, it is then possible to extract the parameters ($g_i^2 D_o$) for each component i with a procedure similar to that set forth above.

What is claimed is:

1. A method for determining a characteristic of formations surrounding an earth borehole, comprising the steps of:
   (a) providing a logging device that is moveable through the borehole;
   (b) producing, from said logging device, a static magnetic field in the formations;
   (c) transmitting, into said formations, from said logging device, a first magnetic pulse sequence and receiving, during said first pulse sequence, magnetic resonance spin echo signals; said first pulse sequence having a portion of a pulse acquisition sequence during which spin echoes are subject to decay due to local magnetic field internal gradients in the formations, and having another portion of the pulse acquisition sequence during which spin echoes are not substantially subject to decay due to said local magnetic field internal gradients in the formations;
   (d) transmitting, into said formations, from said logging device, a second magnetic pulse sequence and receiving, during said second pulse sequence, magnetic resonance spin echo signals; said second pulse sequence having a portion of a pulse acquisition sequence during which spin echoes are subject to decay due to said local magnetic field internal gradients in the formations, and having another portion of the pulse acquisition sequence during which spin echoes are not substantially subject to decay due to said local magnetic field internal gradients in the formations; one of the portions of the pulse acquisition sequence of said second magnetic pulse sequence having at least one different pulse parameter than the corresponding one of the portions of the pulse acquisition sequence of said first magnetic pulse sequence; and
   (e) determining said characteristic of the formations from the spin echo signals of said first pulse sequence and the spin echo signals of said second pulse sequence.

2. The method as defined by claim 1, wherein said different pulse parameter comprises respectively different pulse spacings.

3. The method as defined by claim 1, wherein said different pulse parameter comprises different durations of the respective another portions of the pulse acquisition sequence of the first and second magnetic pulse sequences.

4. The method as defined by claim 1, wherein said portion of the pulse acquisition sequence of said respective first and second magnetic pulse sequences occurs before said another portion of the pulse acquisition sequence of said respective first and second magnetic pulse sequences.

5. The method as defined by claim 2, wherein said portion of the pulse acquisition sequence of said respective first and second magnetic pulse sequences occurs before said another portion of the pulse acquisition sequence of said respective first and second magnetic pulse sequences.

6. The method as defined by claim 1, wherein said portion of the pulse acquisition sequence of said respective first and second magnetic pulse sequences occurs after said another portion of the pulse acquisition sequence of said respective first and second magnetic pulse sequences.

7. The method as defined by claim 3, wherein said portion of the pulse acquisition sequence of said respective first and second magnetic pulse sequences occurs after said another portion of the pulse acquisition sequence of said respective first and second magnetic pulse sequences.

8. The method as defined by claim 1, wherein said portion of the pulse acquisition sequence and said another portion of the pulse acquisition sequence of said respective first and second magnetic pulse sequences comprise successive CPMGs, the CPMG pulse spacing of said portion of the pulse acquisition sequence being much longer than the CPMG pulse spacing of said another portion of the pulse acquisition sequence of said respective first and second magnetic pulse sequences.

9. The method as defined by claim 1, wherein said portion of the pulse acquisition sequence and said another portion of the pulse acquisition sequence of said respective first and second magnetic pulse sequences comprise successive CPMGs, the CPMG pulse spacing of said portion of the pulse acquisition sequence being much longer than the CPMG pulse spacing of said another portion of the pulse acquisition sequence of said respective first and second magnetic pulse sequences.

10. The method as defined by claim 1, wherein said another portion of the pulse acquisition sequence of said respective first and second magnetic pulse sequences is an inversion recovery sequence, and said portion of the pulse acquisition sequence of said respective first and second magnetic pulse sequences is a CPMG.

11. The method as defined by claim 1, wherein said another portion of the pulse acquisition sequence of said respective first and second magnetic pulse sequences is a stimulated echo sequence, and said portion of the pulse acquisition sequence of said respective first and second magnetic pulse sequences is a CPMG.

12. The method as defined by claim 1, wherein said another portion of the pulse acquisition sequence of said respective first and second magnetic pulse sequences is a stimulated echo sequence, and said portion of the pulse acquisition sequence of said respective first and second magnetic pulse sequences is a CPMG.

13. The method as defined by claim 1, wherein said another portion of the pulse acquisition sequence of said respective first and second magnetic pulse sequences is a stimulated echo sequence, and said portion of the pulse acquisition sequence of said respective first and second magnetic pulse sequences is a CPMG.

14. The method as defined by claim 1, wherein said another portion of the pulse acquisition sequence of said respective first and second magnetic pulse sequences is a CPMG, and said portion of the pulse acquisition sequence of said respective first and second magnetic pulse sequences is a Hahn spin echo pulse sequence.

15. The method as defined by claim 14, wherein each of said first and second magnetic pulse sequences includes a repeat of said portion of the pulse acquisition sequence and said another portion of the pulse acquisition sequence after a recovery time $\Delta$.

16. The method as defined by claim 1, wherein said step (e) comprises determining said formation characteristic from spin echo signals of the another portion of the pulse acquisition sequence of said first pulse sequence and spin echo signals of the another portion of the pulse acquisition sequence of said second pulse sequence.

17. The method as defined by claim 1, wherein said step (e) includes deriving a first $T_2$ distribution from said spin echo signals of said first magnetic pulse sequence and deriving a second $T_2$ distribution from said spin echo signals of said second magnetic pulse sequence.

18. The method as defined by claim 2, wherein said step (e) includes deriving a first $T_2$ distribution from said spin echo signals of said first magnetic pulse sequence and deriving a second $T_2$ distribution from said spin echo signals of said second magnetic pulse sequence.

19. The method as defined by claim 16, wherein said step (e) includes deriving a first $T_2$ distribution from said spin echo signals of said first magnetic pulse sequence and deriving a second $T_2$ distribution from said spin echo signals of said second magnetic pulse sequence.

20. The method as defined by claim 17, wherein said step (e) further includes deriving, from said first and second $T_2$ distributions, at particular values of $T_2$, the product $g^2D$ where g is magnetic field gradient and D is the diffusion constant of the formation fluid.

21. The method as defined by claim 18, wherein said step (e) further includes deriving, from said first and second $T_2$ distributions, at particular values of $T_2$, the product $g^2D$ where g is magnetic field gradient and D is the diffusion constant of the formation fluid.

22. The method as defined by claim 17 wherein said step (e) includes deriving a formation pore size distribution from said spin echo signals of said first pulse sequence and the spin echo signals of said second pulse sequence.

23. The method as defined by claim 20, wherein said step (e) further includes deriving a formation pore size distribution from values of $g^2D$.

24. The method as defined by claim 1, wherein said step (e) includes deriving a formation local gradient from the spin echo signals of the first magnetic pulse sequence and the spin echo signals of the second magnet pulse sequence.

25. The method as defined by claim 1, wherein said step (e) includes deriving formation permeability from the spin echo signals of said first pulse echo sequence and the spin echo signals of said second pulse echo signals.

26. The method as defined by claim 17, wherein said step (e) includes deriving formation permeability from the spin echo signals of said first pulse echo sequence and the spin echo signals of said second pulse echo signals.

27. The method as defined by claim 20, wherein said step (e) further includes deriving formation permeability from values of $g^2D$.

28. The method as defined by claim 21, wherein said step (e) further includes deriving formation permeability from values of $g^2D$.

29. The method as defined by claim 21, wherein said step (e) further includes deriving the diffusion constant D of formation fluids from values of $g^2D$.

30. The method as defined by claim 28, wherein said step (e) further includes deriving the diffusion constant D of formation fluids from values of $g^2D$.

31. The method as defined by claim 8, wherein each of said first and second magnetic pulse sequences is of the form: $\pi/2$-$\tau/2n$-$\pi$-$\tau/2n$-echo-$\tau/2n$-$\pi$-$\tau/2n$-echo .... echo-$\Delta t/2\pi$-$\Delta t/2$-echo-$\Delta t/2$-$\pi$-$\Delta t/2$-echo ....

32. The method as defined by claim 10, wherein each of said first and second magnetic pulse sequences is of the form: $\pi$-t-$\pi/2$-$\tau/2n$-$\pi$-$\tau/2n$-echo-$\tau/2n$ .... $\pi$-$\tau/2n$-signal detection.

33. The method as defined by claim 11, wherein said second magnetic pulse sequences is of the form: $n/2$-$\delta$-$\pi/2$-($\Delta$-$\delta$)-$\pi/2$-$\delta$(stimulated echo)-$\Delta t/2$-$\pi$-$\Delta t/2$-(echo)-$\Delta t/2$-$\pi$-$\Delta t/2$-(echo) ....

34. The method as defined by claim 1, further comprising the transmitting, into said formations at least one further magnetic pulse sequence and receiving, during said further pulse sequence, magnetic resonance spin echoes, said further pulse sequence having a portion of a pulse acquisition sequence during which spin echoes are subject to decay due to said local magnetic field internal gradients in the formations, and having another portion of the pulse acquisition sequence during which spin echoes are not substantially subject to decay due to said local magnetic field internal gradients; one of the portions of the pulse acquisition sequence of said further magnetic pulse sequence having at least one different pulse parameter than the corresponding ones of the portion of the pulse acquisition sequence of said first and second magnetic pulse sequences, and where in said step (e) comprises determining said characteristic of the formations from the spin echo signals of said first pulse sequence, and the spin echo signals of said second pulse sequence, and the spin echo signals of said at least one further pulse sequence.

35. The method as defined by claim 2, further comprising the transmitting, into said formations at least one further magnetic pulse sequence and receiving, during said further pulse sequence, magnetic resonance spin echoes, said further pulse sequence having a portion of a pulse acquisition sequence during which spin echoes are subject to decay due to said local magnetic field internal gradients in the formations, and having another portion of the pulse acquisition sequence during which spin echoes are not substantially subject to decay due to said local magnetic field internal gradients; one of the portions of the pulse acquisition sequence of said further magnetic pulse sequence having at least one different pulse parameter than the corresponding ones of the portion of the pulse acquisition sequence of said first and second magnetic pulse sequences, and wherein said step (e) comprises determining said characteristic of the formations from the spin echo signals of said first pulse sequence, and the spin echo signals of said second pulse sequence, and the spin echo signals of said at least one further pulse sequence.

36. A method for determining a characteristic of formations surrounding an earth borehole, comprising the steps of:
(a) providing a logging device that is moveable through the borehole;
(b) producing, from said logging device, a static magnetic field in the formations;
(c) transmitting, into said formations, from said logging device, a magnetic pulse sequence and receiving, during said pulse sequence, magnetic resonance spin echo signals; said magnetic pulse sequence having a portion of a pulse acquisition sequence with relatively long pulse spacing times $t_{E,1}$ and another portion of the pulse acquisition sequence with relatively short pulse spacing times $t_{E,2}$; and (d) repeating step (c) with pulse spacing times $t_{E,2}$ that are different than $t_{E,2}$;

(e) deriving respective $T_2$ distributions from the spin echo signals obtained during said another portion of the pulse acquisition sequence of step (c) and during said another portion of the pulse acquisition sequence of step (d); and (f) determining said characteristic of said formations from said respective $T_2$ distributions.

37. The method as defined by claim 36, wherein said portion of the pulse acquisition sequence and said another portion of the pulse acquisition sequence of the pulse sequence of step (c) are CPMGs.

38. The method as defined by claim 36, wherein said step (f) includes deriving, from the respective $T_2$ distributions, the product $g^2D$ where g is magnetic field gradient and D is the diffusion constant of the formation fluid.

39. The method as defined by claim 37, wherein said step (f) includes deriving, from the respective $T_2$ distributions, the product $g^2D$ where g is magnetic field gradient and D is the diffusion constant of the formation fluid.

40. The method as defined by claim 38, wherein said step (f) further includes deriving a formation pore size distribution from values of $g^2D$.

41. The method as defined by claim 38, wherein said step (f) further includes deriving formation permeability from values of $g^2D$.

* * * * *